(12) United States Patent
George

(10) Patent No.: US 11,191,559 B2
(45) Date of Patent: Dec. 7, 2021

(54) SPECIMEN RETRIEVAL DEVICE

(71) Applicant: Covidien LP, Mansfield, MA (US)

(72) Inventor: Sabastian Koduthully George, Hyderabad (IN)

(73) Assignee: Covidien LP, Mansfield, MA (US)

(*) Notice: Subject to any disclaimer, the term of this patent is extended or adjusted under 35 U.S.C. 154(b) by 280 days.

(21) Appl. No.: 16/517,710

(22) Filed: Jul. 22, 2019

(65) Prior Publication Data
US 2020/0085455 A1  Mar. 19, 2020

Related U.S. Application Data

(60) Provisional application No. 62/733,095, filed on Sep. 19, 2018.

(51) Int. Cl.
*A61B 17/221* (2006.01)
*A61B 17/34* (2006.01)
*A61B 17/00* (2006.01)

(52) U.S. Cl.
CPC ...... *A61B 17/221* (2013.01); *A61B 17/00234* (2013.01); *A61B 17/3423* (2013.01); *A61B 2017/00287* (2013.01)

(58) Field of Classification Search
CPC ............ A61B 17/00234; A61B 17/221; A61B 17/3423; A61B 2017/00287; A61B 2017/00991
See application file for complete search history.

(56) References Cited

U.S. PATENT DOCUMENTS

| 30,471 | A | 10/1860 | Dudley |
| 35,164 | A | 5/1862 | Logan et al. |
| 156,477 | A | 11/1874 | Bradford |
| 1,609,014 | A | 11/1926 | Dowd |
| 3,800,781 | A | 4/1974 | Zalucki |

(Continued)

FOREIGN PATENT DOCUMENTS

| DE | 3542667 A1 | 6/1986 |
| DE | 8435489 U1 | 8/1986 |

(Continued)

OTHER PUBLICATIONS

European Search Report EP 12191639.9 dated Feb. 20, 2013.
(Continued)

*Primary Examiner* — Mohamed G Gabr
(74) *Attorney, Agent, or Firm* — Carter, DeLuca & Farrell LLP

(57) ABSTRACT

A specimen retrieval device includes a tubular body, an inner shaft slidably positioned within a longitudinal bore of the tubular body, and a specimen bag supported on the distal portion of the inner shaft. The specimen bag includes an open end, a body, a closed portion, and an inner surface, the body of the specimen bag including a plurality of folds between the open end and the closed portion, the plurality of folds being movable from a folded state to an unfolded state to increase a volume of the specimen bag. The specimen bag also includes a release string secured to the plurality of folds, the release string movable from a non-actuated position to an actuated position to sequentially release at least one of the plurality of folds from the folded state to the unfolded state to increase the volume of the bag.

16 Claims, 8 Drawing Sheets

(56) References Cited

U.S. PATENT DOCUMENTS

| | | |
|---|---|---|
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinsk et al. |
| 8,206,401 B2 | 6/2012 | Nakao |
| 8,337,510 B2 | 12/2012 | Rieber et al. |
| 8,343,031 B2 | 1/2013 | Gertner |

(56) References Cited

U.S. PATENT DOCUMENTS

| | | |
|---|---|---|
| 8,348,827 B2 | 1/2013 | Zwolinsk |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0256425 A1 | 11/2005 | Prusiner |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0255597 A1 | 10/2008 | Pravong et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0158010 A1* | 6/2012 | Menn ............... A61B 17/00234 606/114 |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0184536 A1 | 7/2013 | Shibley et al. |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |
| 2017/0049427 A1 | 2/2017 | Do et al. |
| 2017/0215904 A1 | 8/2017 | Wassef et al. |
| 2017/0224321 A1 | 8/2017 | Kessler et al. |
| 2017/0325798 A1 | 11/2017 | Prior |

FOREIGN PATENT DOCUMENTS

| | | |
|---|---|---|
| DE | 4204210 A1 | 8/1992 |
| DE | 19624826 A1 | 1/1998 |
| DE | 10327106 A1 | 12/2004 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |
| WO | 2011090866 A2 | 7/2011 |
| WO | 2013075103 A1 | 5/2013 |
| WO | 2014134285 A1 | 9/2014 |
| WO | 2015134888 A1 | 9/2015 |
| WO | 2015164591 A1 | 10/2015 |
| WO | 2017189442 A1 | 11/2017 |
| WO | 2018148744 A1 | 8/2018 |

OTHER PUBLICATIONS

European Search Report EP 11250837.9 dated Sep. 10, 2013.
European Search Report EP 11250838.7 dated Sep. 10, 2013.

(56) References Cited

OTHER PUBLICATIONS

European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Feb. 12, 2019 issued in EP Application No. 18208634.
International Search Report issued in Appl. No. PCT/US2018/058609 dated Feb. 22, 2019.
Extended European Search Report issued in Appl. No. EP 19197987.1 dated Jan. 8, 2020 (10 pages).

* cited by examiner

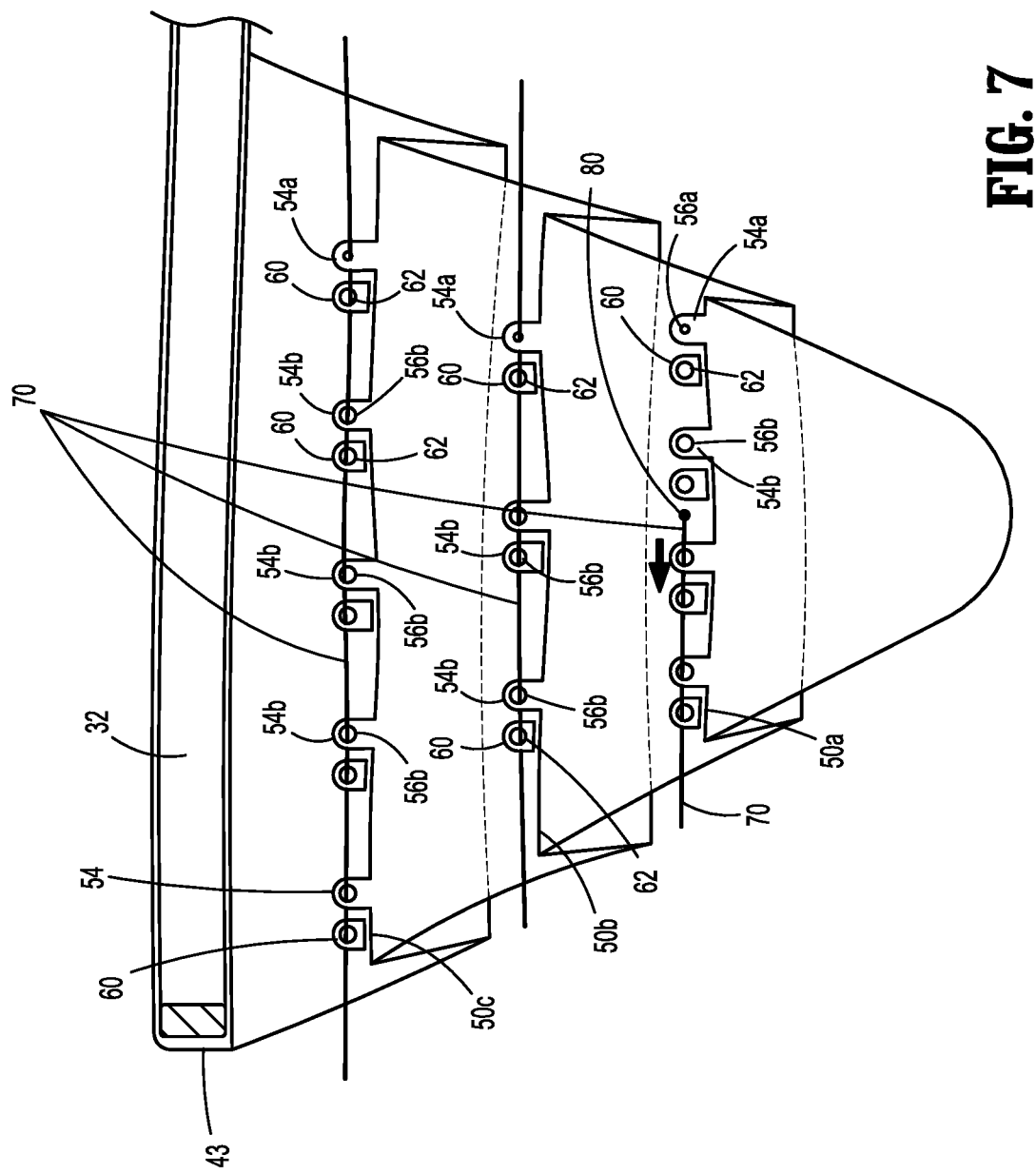

SPECIMEN RETRIEVAL DEVICE

CROSS-REFERENCE TO RELATED APPLICATION

This application claims the benefit of and priority to U.S. Provisional Patent Application No. 62/733,095 filed Sep. 19, 2018, the entire disclosure of which is incorporated by reference herein.

TECHNICAL FIELD

The present disclosure relates generally to surgical apparatuses for use in minimally invasive surgical procedures, such as endoscopic and/or laparoscopic procedures, and more particularly, the present disclosure relates to a surgical apparatus including a specimen retrieval device for collecting body tissue(s) and/or body fluid(s) during these procedures.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit the visual inspection and magnification of a body cavity. The surgeon can then perform diagnostic and/or therapeutic procedures at the surgical site with the aid of specialized instrumentation, such as forceps, graspers, cutters, applicators, and the like, which are designed to fit through additional cannulas.

When removing certain tissues from the body cavity, for example tumor tissue, it is important that the tumor tissue does not come into contact with healthy or uninvolved tissue. If tumor tissue or tissue parts have to be removed, they may be introduced into an "extraction bag," also referred to herein as a "specimen bag," at the site where the tumor or diseased tissue has been detached from the surrounding tissue, after which the specimen bag is withdrawn from the body, thereby minimizing contact of the diseased tissue with healthy tissue.

Improved specimen bags for use in minimally invasive surgical procedures remain desirable.

SUMMARY

The present disclosure is directed to surgical apparatuses and methods for their use in minimally invasive surgery. In embodiments, the present disclosure is directed to a specimen retrieval device including a tubular body defining a longitudinal bore, the tubular body having a proximal portion, a distal portion, and a hand grip supported on the proximal portion of the tubular body. The specimen retrieval device also includes an inner shaft having a proximal portion, a distal portion, an actuation handle supported on the proximal portion of the inner shaft, and a support member extending from a distal portion of the inner shaft. The specimen retrieval device further includes a specimen bag supported on the support member at the distal portion of the inner shaft, the specimen bag including an open end, a body, a closed portion, and an inner surface, the body of the specimen bag including a plurality of folds between the open end and the closed portion, the plurality of folds being movable from a folded state to an unfolded state to increase a volume of the specimen bag, and a release string secured to the plurality of folds, the release string movable from a non-actuated position to an actuated position to sequentially release at least one of the plurality of folds from the folded state to the unfolded state to increase the volume of the bag.

In embodiments, the inner surface of the specimen bag includes flanges attached thereto, each flange having a hole therein, and the plurality of folds each include flanges extending therefrom, each flange having a hole therein.

In some embodiments, the release string has a knot at a distal portion thereof.

In other embodiments, a first hole in a first flange extending from each of the plurality of folds furthest from the distal portion of the inner shaft is of a smaller diameter compared with the holes in the remaining flanges extending from the plurality of folds.

In embodiments, the plurality of folds is from two folds to ten folds.

In some embodiments, the plurality of folds includes two folds.

In other embodiments, the plurality of folds includes three folds.

In yet other embodiments, the plurality of folds includes five folds. In embodiments, the adjustable volume specimen bag permits the formation of a specimen bag of varying volumes of 250 ml, 500 ml, 1000 ml, 1200 ml and 1500 ml.

In some embodiments, the support member includes a pair of resilient fingers which support the specimen bag and open the open end of the specimen bag in the deployed state.

In other embodiments, the resilient fingers are positioned adjacent the open end of the specimen bag to open the specimen bag when the specimen retrieval device is in the deployed state.

Methods of the present disclosure include, in embodiments, introducing a tubular body of a specimen retrieval device through a body opening into a body cavity; moving an inner shaft including a support member within a longitudinal bore of the tubular body to position a specimen bag supported on the support member within the body cavity; and withdrawing a release string from the specimen bag to incrementally increase a volume of the specimen bag.

In embodiments, withdrawing the release string from the specimen bag includes proximally pulling the release string so that the release string passes through holes on flanges extending from a plurality of folds on the specimen bag and holes on flanges extending from an inner surface of the specimen bag.

In some embodiments, withdrawing the release string from the specimen bag includes proximally pulling the release string so that the release string passes through holes on flanges extending from at least one fold of the plurality of folds on the specimen bag and holes on flanges extending from an inner surface of the specimen bag.

In embodiments, the method of the present disclosure further includes passing a tissue specimen through an opening of the specimen bag into the specimen bag; and removing the specimen retrieval device from the body cavity.

In some embodiments, the method further includes closing the opening of the specimen bag before removing the specimen retrieval device from the body cavity.

In other embodiments, closing the opening of the specimen bag occurs by proximally pulling a pull string extending about the opening of the specimen bag.

BRIEF DESCRIPTION OF THE DRAWINGS

Various embodiments of the presently disclosed specimen retrieval device are described herein below with reference to the drawings, wherein:

FIG. 7 is a side view of the specimen bag shown in FIG. 6, showing the movement of a release string during deployment of the specimen bag;

DETAILED DESCRIPTION OF EMBODIMENTS

Figure 1:
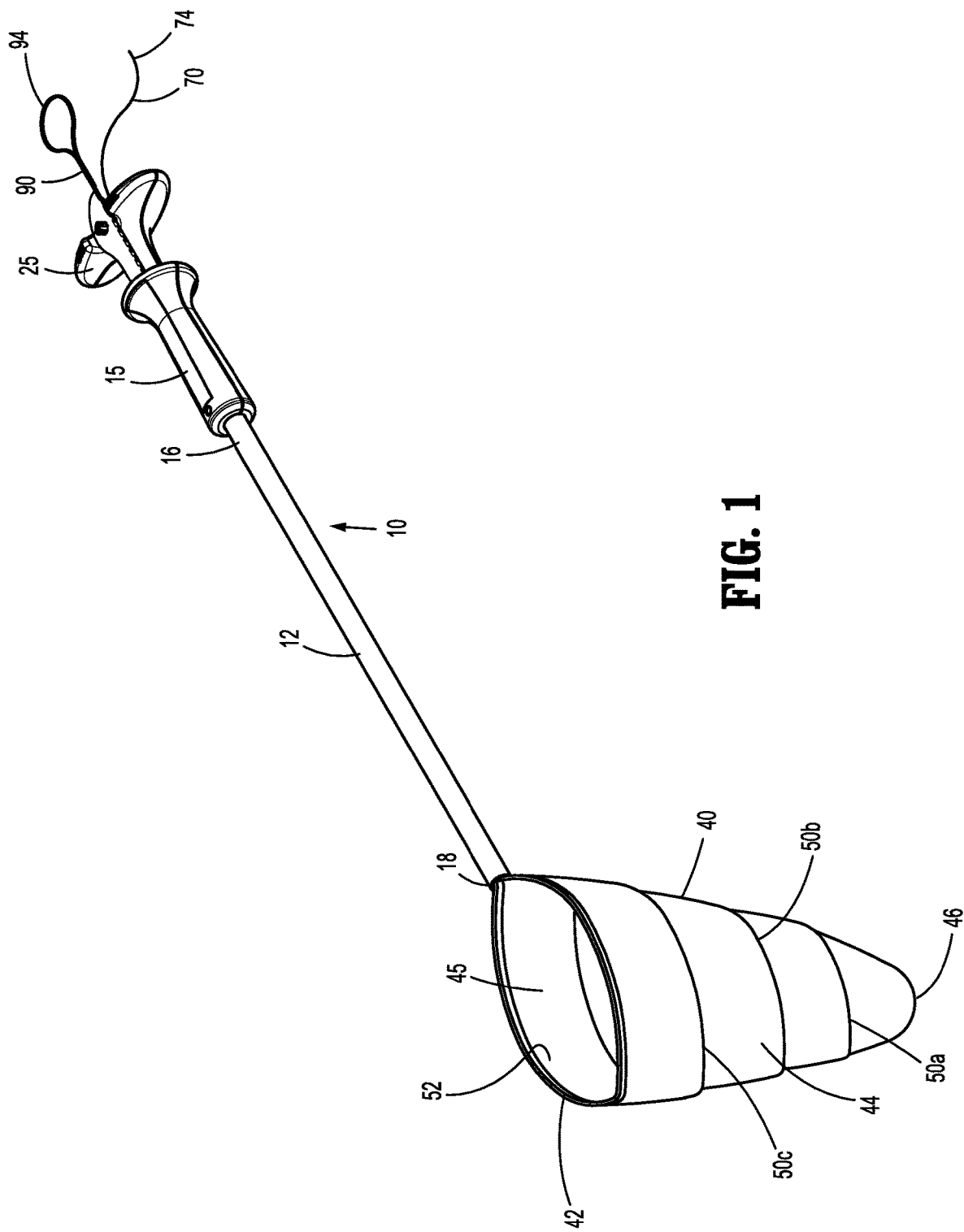
FIG. 1 is a side perspective view of an exemplary embodiment of the presently disclosed specimen retrieval device in a deployed state.

The present disclosure provides a specimen retrieval device for use in minimally invasive surgical procedures. As used herein with reference to the present disclosure, minimally invasive surgical procedures encompass laparoscopic procedures, arthroscopic procedures, and endoscopic procedures, and refer to procedures utilizing scopes or similar devices having relatively narrow operating portions capable of insertion through a small incision in the skin.

The aspects of the present disclosure may be modified for use with various methods for retrieving tissue specimens during minimally invasive surgical procedures, sometimes referred to herein as minimally invasive procedures. Examples of minimally invasive procedures include, for example, cholecystectomies, appendectomies, nephrectomies, colectomies, splenectomies, and the like.

The presently disclosed specimen retrieval device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. The term "clinician" is used generally to refer to medical personnel including doctors, surgeons, nurses, and support personnel.

Figure 2:
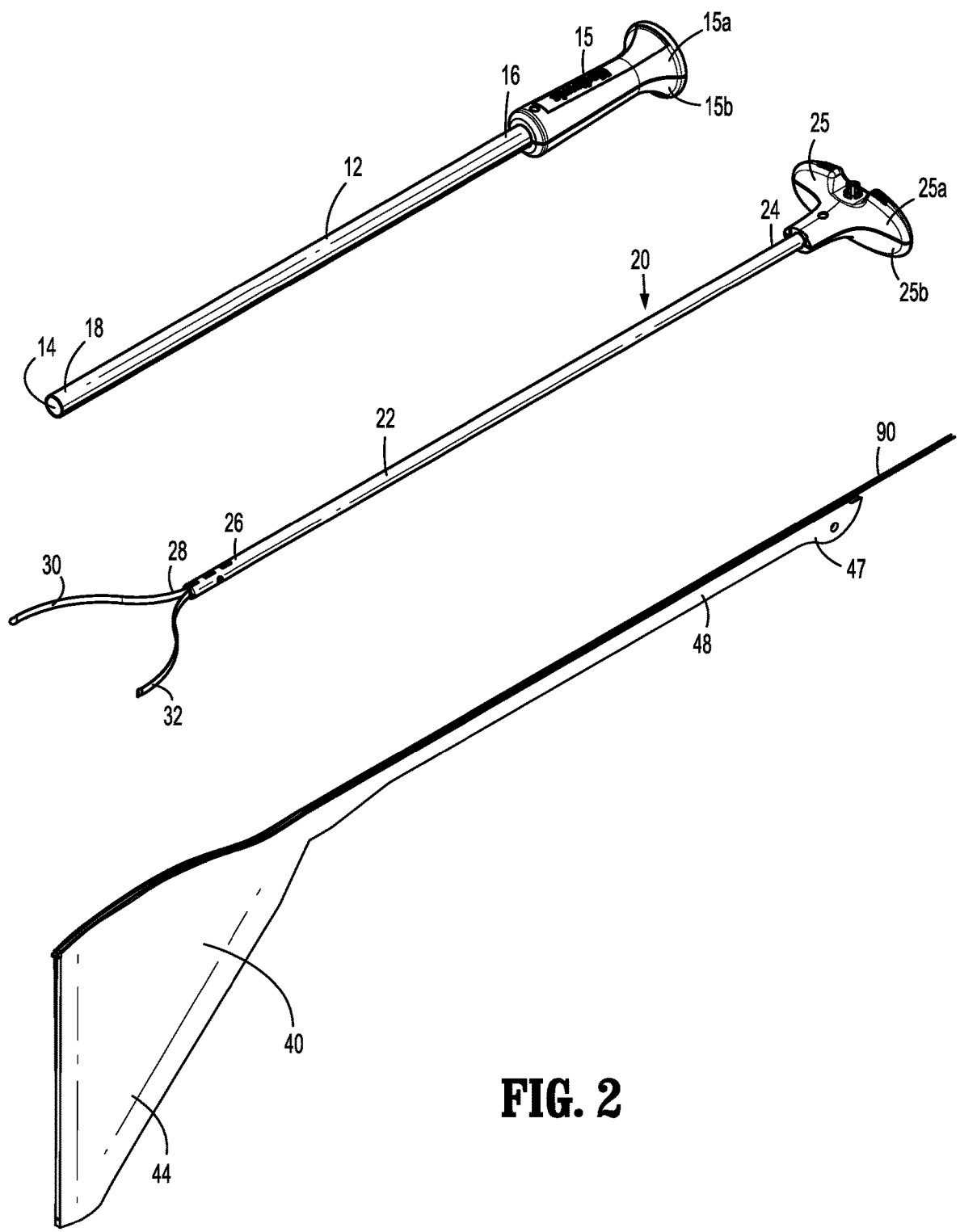
FIG. 2 is an exploded view of the specimen retrieval device shown in FIG. 1.

Referring to FIGS. 1-11, and initially with reference to FIGS. 1 and 2, the specimen retrieval device 10 of the present disclosure includes a tubular body 12 having a proximal portion 16 and a distal portion 18, and defining a longitudinal bore 14 (FIG. 2) that extends between the proximal portion 16 and the distal portion 18. The proximal portion of the tubular body 12 supports a hand grip 15. The specimen retrieval device 10 also includes an inner shaft assembly 20 (FIG. 2) including an inner shaft 22 slidably positioned within the longitudinal bore 14 of the tubular body 12, an actuation handle 25 secured to a proximal portion 24 of the inner shaft 22, and an adjustable volume specimen bag 40 (FIG. 1) supported on a distal portion 26 of the inner shaft 22.

The hand grip 15 on the tubular body 12 may be formed as a unitary component or, as depicted in FIG. 2, as two separate half components 15a, 15b, that are coupled to one another about the tubular body 12 by one or more suitable coupling methods (e.g., one or more suitable adhesives). In the latter instance, an indent/detent configuration (not shown) may be utilized to facilitate coupling the two separate half components 15a, 15b to one another.

The actuation handle 25 on the inner shaft 22 may likewise be formed as a unitary component or, in embodiments, as depicted in FIG. 2, as two separate half components 25a, 25b that are coupled to one another by one or more suitable coupling methods (e.g., one or more suitable adhesives).

The tubular body 12 and/or the inner shaft assembly 22 of the present disclosure are made of biocompatible materials within the purview of those skilled in the art, in embodiments, polymeric materials. For example, the tubular body 12 and/or the inner shaft assembly 22 may be made of polycarbonates or thermoplastic polyurethanes sold under the name PELLETHANE®, which offer flexibility and a wide range of hardness. The tubular body 12 and/or the inner shaft assembly 22, for example, may be fabricated from PELLETHANE® 2363-80A, PELLETHANE® 2363-90A, PELLETHANE® 2363-55D, any combination thereof, or any alternatives within the purview of those skilled in the art.

In some embodiments, the tubular body 12 and the inner shaft assembly 22 are formed of the same material. In other embodiments, the tubular body 12 and the inner shaft assembly 22 are formed of different materials.

The adjustable volume specimen bag 40 includes a body 44 having a generally tubular or elongated configuration that is defined by an openable and closable portion (or mouth) 42 and a closed portion 46 (FIG. 1). The closable portion 42 defines an opening 45. Alternatively, other specimen bag configurations are envisioned. As described in greater detail below, the body of the specimen bag includes a plurality of folds between the opening 45 and the closed portion 46, the plurality of folds being movable from a folded state to an unfolded state to increase the volume of the specimen bag.

The body 44 of the adjustable volume specimen bag 40 may be made from any suitable biocompatible material (e.g., nylon, urethane, ripstop nylon or latex) capable of forming a flexible collapsible member, or membrane. In embodiments, the material from which the adjustable volume specimen bag 40 is made is resilient, antistatic, pyrogen-free, non-toxic, and sterilizable. The adjustable volume specimen bag 40 may be opaque or clear. In some embodiments, the body 44 of the adjustable volume specimen bag 40 is formed of a nylon material, or combinations of nylon materials.

Referring to FIG. 2, the distal portion 26 of the inner shaft 22 is coupled to a support member 28 that is configured to support the mouth 42 of the adjustable volume specimen bag 40. In embodiments, the support member 28 includes a pair of resilient fingers 30, 32 that extend distally from the distal portion 26 of the inner shaft 22. In embodiments, the resilient fingers 30, 32 can be integrally formed with the distal portion 26 of the inner shaft 22 such as by molding. Alternatively, a retention pin (not shown) may be used to attach the resilient fingers 30, 32 to the distal portion 26 of the inner shaft 22. The resilient fingers 30, 32 are movable from a spaced non-deformed state shown in FIG. 2 to a deformed state (not shown) to facilitate placement of the adjustable volume specimen bag 40 into the tubular body 12.

The resilient fingers 30, 32 return to the non-deformed state (FIG. 2) when the adjustable volume specimen bag 40 is deployed from the tubular body 12 to open the opening 45 of the closable portion 42 of the adjustable volume specimen bag 40, as described below.

In an assembled configuration, the hand grip 15 and the actuation handle 25 can be manipulated to facilitate manipulation of the specimen retrieval device 10 and the sliding of the inner shaft 22 within the tubular body 12. More specifically, the hand grip 15 can be grasped by the clinician with one hand and the actuation handle 25 can be grasped by the clinician with the other hand to move the inner shaft 22 within the tubular body 12.

Figure 6:
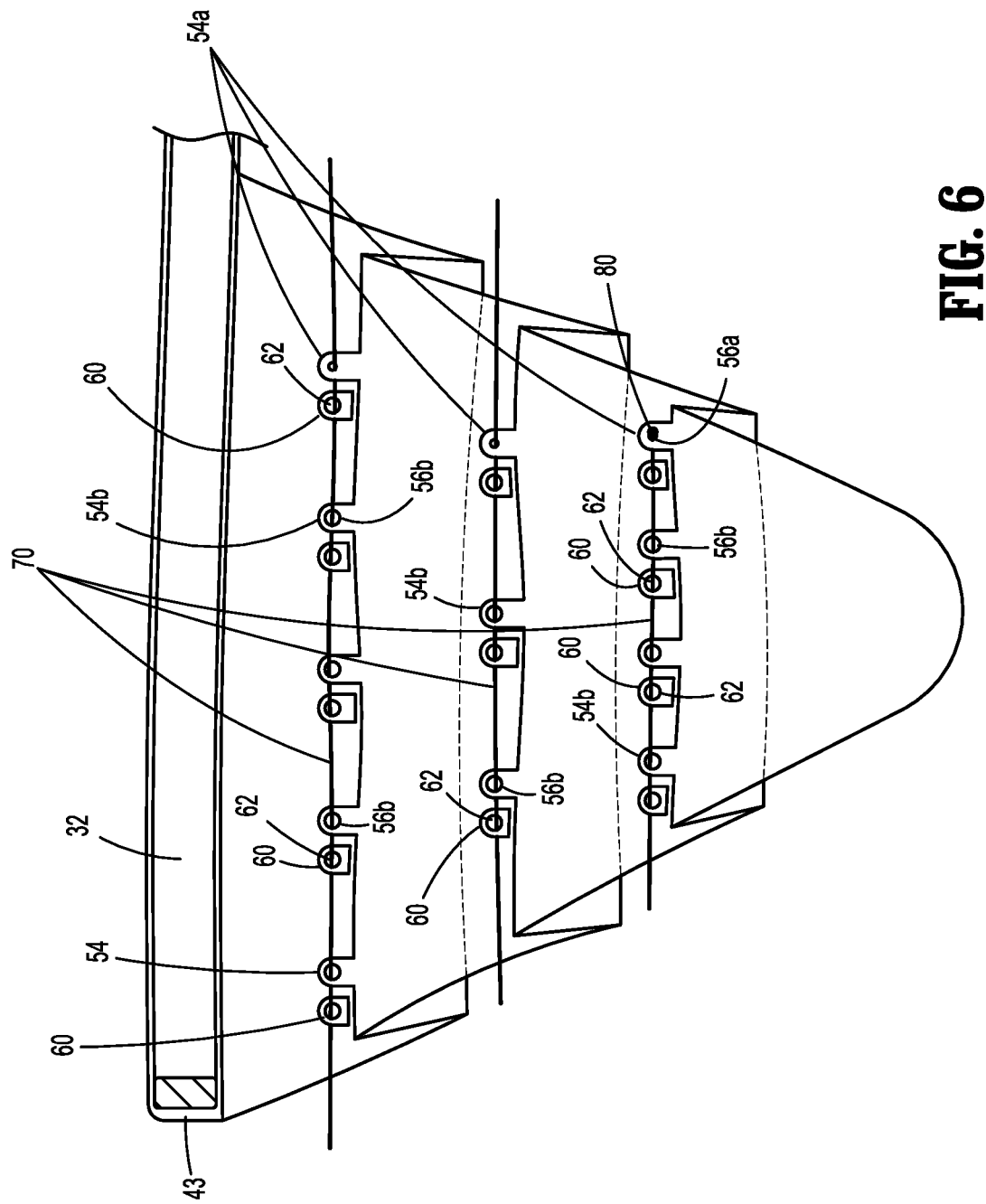
FIG. 6 is a cross-sectional view taken along section line 6-6 of FIG. 3, showing the configuration of the specimen bag prior to folding of the specimen bag and prior to deployment.

In embodiments, the mouth 42 of the adjustable volume specimen bag 40 has a pull string 90 attached thereto (FIG. 1), as well as resilient fingers 30, 32 attached thereto. In other embodiments, the resilient fingers 30, 32 and the pull string 90 may be received in a cuff 43 formed at the mouth 42 of the adjustable volume specimen bag 40. (FIG. 6 shows a single resilient finger 32 within the cuff 43.)

In use, the tubular body 12 of the specimen retrieval device 10 can be inserted through an incision (not shown) with the adjustable volume specimen bag 40 furled about the inner shaft 22 and positioned within the tubular body 12 to position the adjustable volume specimen bag 40 in a body cavity adjacent a surgical site. When the tubular body 12 is properly positioned, the clinician can grip the hand grip 15.

The clinician then pushes the actuation handle 25 (FIG. 2) on the proximal portion 24 of the inner shaft 22 distally in relation to the hand grip 15 and the tubular body 12 (not shown), so the distal portion 26 of the inner shaft 22, including the adjustable volume specimen bag 40, exits the distal portion 18 of the tubular body 12 (FIG. 1). Once the adjustable volume specimen bag 40 has exited the tubular body 12, the resilient fingers 30, 32 (FIG. 4) return to their non-deformed state, thereby opening the mouth 42 of the adjustable volume specimen bag 40 to ensure the adjustable volume specimen bag 40 is deployed.

Figure 3:
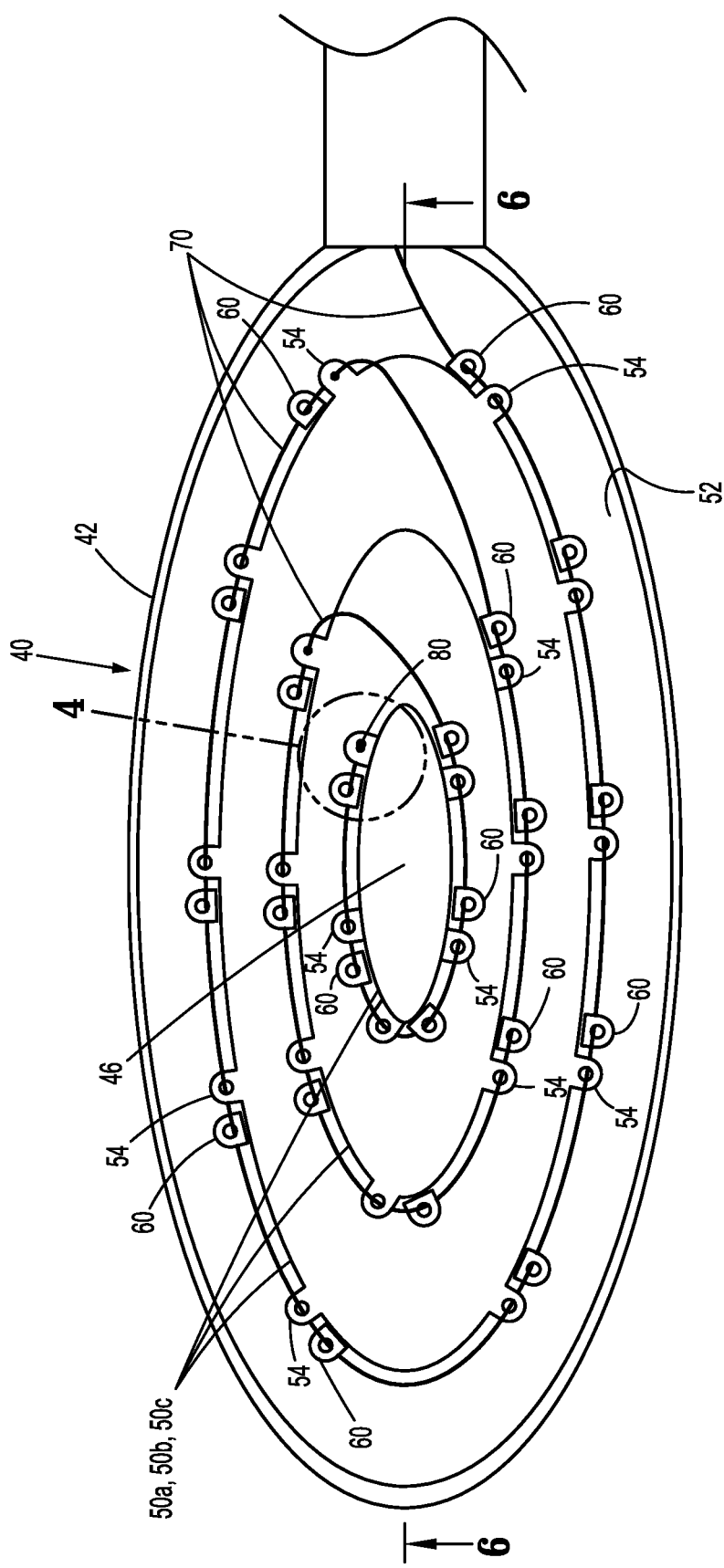
FIG. 3 is a side perspective view of a specimen bag of the specimen retrieval device shown in FIG. 1 prior to deployment.
Figure 4:
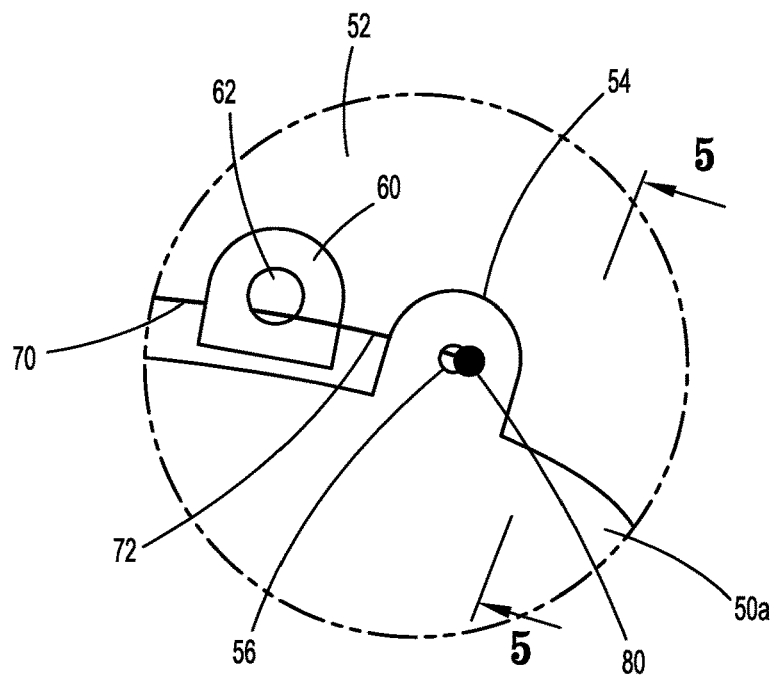
FIG. 4 is an enlarged view of the indicated area of detail shown in FIG. 3.

Turning to FIGS. 3-11, the adjustable volume specimen bag 40 of the present disclosure will be described in greater detail. As shown in FIGS. 3 and 4, the adjustable volume specimen bag 40 has multiple folds 50a, 50b, 50c so that it can lay flat. While FIG. 3 depicts a first fold 50a, a second fold 50b, and a third fold 50c, any number of folds may be used to produce the adjustable volume specimen bag 40 of the present disclosure. For example, in embodiments the adjustable volume specimen bag 40 may have from two folds to ten folds (not shown).

The inner surface 52 of the adjustable volume specimen bag 40 has flanges 60 thereon, each flange 60 having a hole 62 therein. Flanges 54 also extend from the folds 50a, 50b, and 50c of the adjustable volume specimen bag 40. Each flange 54 has a hole 56 therein.

As shown in FIG. 3, the folds 50a, 50b, and 50c of the adjustable volume specimen bag 40 start near the closed portion 46 of the adjustable volume specimen bag 40 and radially extend to the mouth 42 of the adjustable volume specimen bag 40 so that the flanges 54 and 60 form a series of concentric circles.

As shown in FIGS. 3-4, the adjustable volume specimen bag 40 also has a release string 70 having a knot 80 (FIG. 4) at a distal portion 72 of the release string 70 (FIG. 1). The release string 70 passes through holes 62 in flanges 60 on the inner surface 52 of the adjustable volume specimen bag 40, as well as the holes 56 in the flanges 54 extending from the folds 50a, 50b, and 50c of the adjustable volume specimen bag 40. As shown in FIG. 1, the release string 70 passes through the handle 15 of the specimen retrieval device 10 and emerges from the handle 15 with proximal portion 74 of the release string 70 free.

Figure 5:
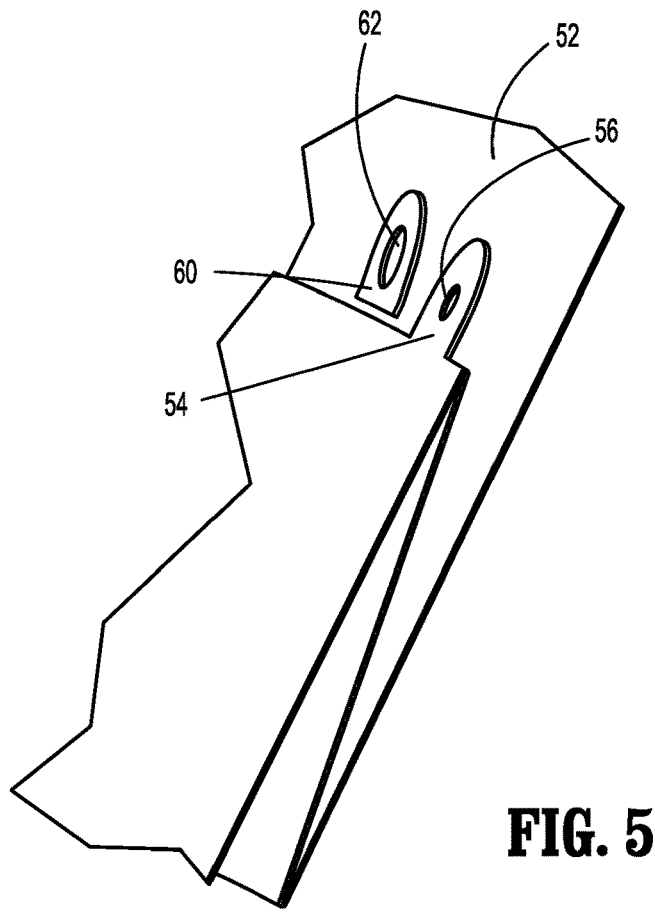
FIG. 5 is a side view of the area of detail shown in FIG. 4.

As shown in greater detail in FIGS. 4 and 5, the holes 56a in the flanges 54a closest to the closed portion 46 of the adjustable volume specimen bag 40 extending from each fold 50a, 50b and 50c are of a smaller diameter than the holes 62 in the flanges 60 on the inner surface 52 of the adjustable volume specimen bag 40 and the other holes 56b in the flanges 54b extending from each fold 50a, 50b and 50c of the adjustable volume specimen bag 40. The knot 80 at the distal portion 72 of the release string 70 will pass easily through the holes 62 in flanges 60 on the inner surface 52 of the adjustable volume specimen bag 40 and the other holes 56b in the flanges 54b extending from the folds 50a, 50b and 50c. Thus, the knot 80 at the distal portion 72 of the release string 70 will be larger than the diameter of the hole 56a in the flange 54a closest to the closed portion 46 of the adjustable volume specimen bag 40 extending from the folds 50a, 50b and 50c; the knot 80 may pass through the hole 56a in the flange 54a closest to the closed portion 46 of the adjustable volume specimen bag 40 extending from the folds 50a, 50b and 50c, but will require the clinician to exert greater tension on the release string 70 to have the knot 80 pass through the hole 56a in the flange 54a closest to the closed portion 46 of the adjustable volume specimen bag 40 extending from the folds 50a, 50b and 50c.

As shown in FIG. 6, before use, the knot 80 at the distal portion 72 of the release string 70 is retained adjacent the hole 56a closest to the closed portion 46 of the adjustable volume specimen bag 40.

Figure 8:
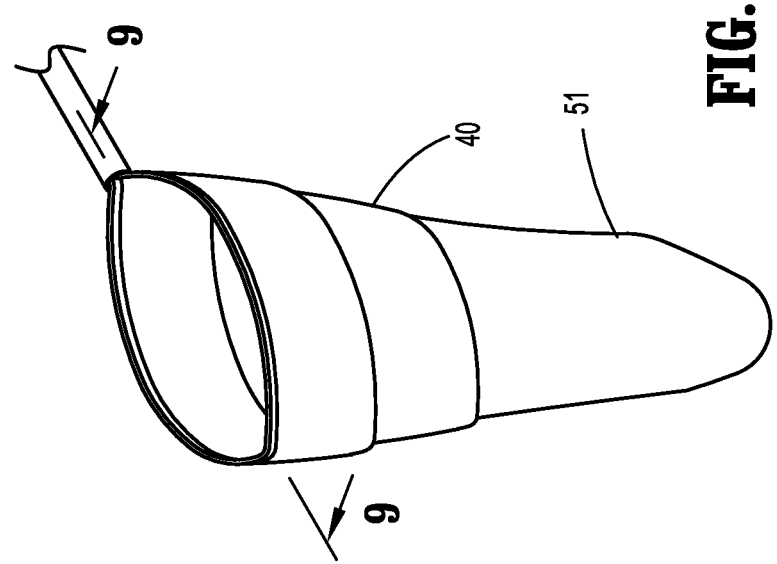
FIG. 8 is a side perspective view of the specimen retrieval device shown in FIG. 1, showing the specimen bag after a first bottom fold of the specimen bag has unfolded as depicted in FIG. 7, producing a specimen bag of a first size.

In use, the proximal portion of the specimen retrieval device 10 is introduced into a patient so that the folded adjustable volume specimen bag 40 is deployed within the patient. The clinician proximally pulls the pull ring 90 (FIG. 1) to provide tension on the release string 70 (FIG. 1). In order to produce a desired size of the adjustable volume specimen bag 40, proximally pulling the release string 70 with sufficient force will pull the knot 80 at the distal portion 72 of the release string 70 through the hole 56a in the flange 54a closest to the closed portion 46 of the adjustable volume specimen bag 40 extending om the first fold 50a. Continuing to proximally pull the release string 70 (indicated by arrow "A" in FIG. 7) will pull the release string 70 and the knot 80 at the distal portion 72 of the release string 70 through the remaining holes 56b in the flanges 54b extending from the first fold 50a, as well as the holes 62 in the flanges 60 on the inner surface 52 of the adjustable volume specimen bag 40 adjacent the first fold 50a, until the knot 80 reaches the first hole 56a in the first flange 54a on the second fold 50b. Once the release string 70 passes through the remaining holes 56b associated with the first fold 50a, the first fold 50a is no longer held in place by the release string 70 and unfolds to form the adjustable volume specimen bag 40 of a first size "S1". (FIG. 8).

Figure 9:
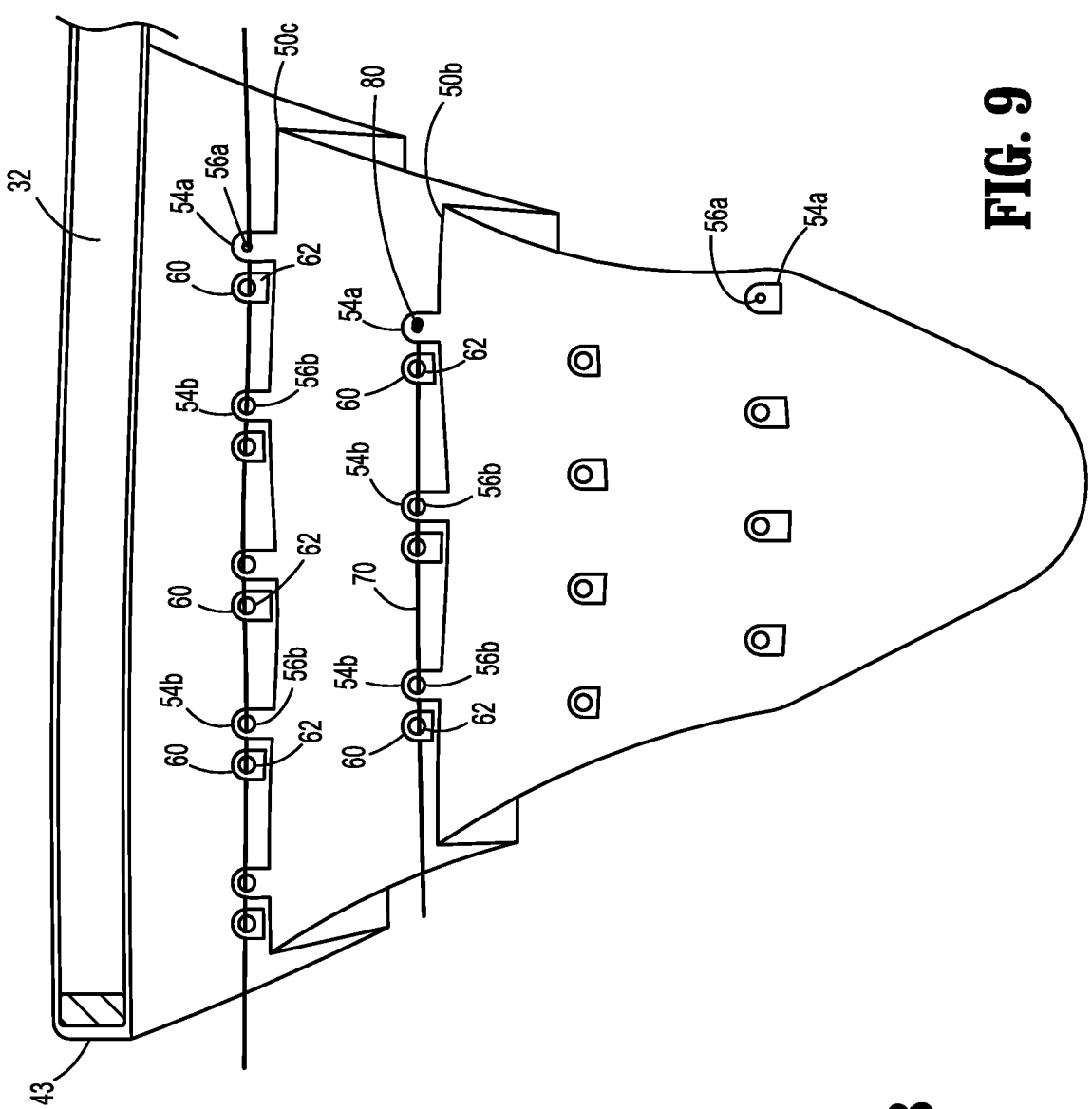
FIG. 9 is a cross-sectional view taken along section line 9-9 of FIG. 8.

As shown in FIG. 9, the first hole 56a extending from the first flange 54a on the second fold 50b will stop the knot 80 at the distal portion 72 of the release string 70 from passing therethrough, at which point the clinician will decide whether or not to continue to proximally pull the release string 70 to increase the volume of the adjustable volume specimen bag 40. In this case, the knot 80 stopping the movement of the release string 70 at the first hole 56a in the first flange 54a on the second fold 50b provides the clinician with feedback of the expansion of the adjustable volume specimen bag 40.

If the size of a tissue specimen to be removed from a patient can fit into the adjustable volume specimen bag 40 of the first size "S1", then the clinician will stop proximally pulling the release string 70, and the specimen retrieval device 10, having the tissue specimen within the adjustable volume specimen bag 40, may be removed from the patient.

Figure 10:
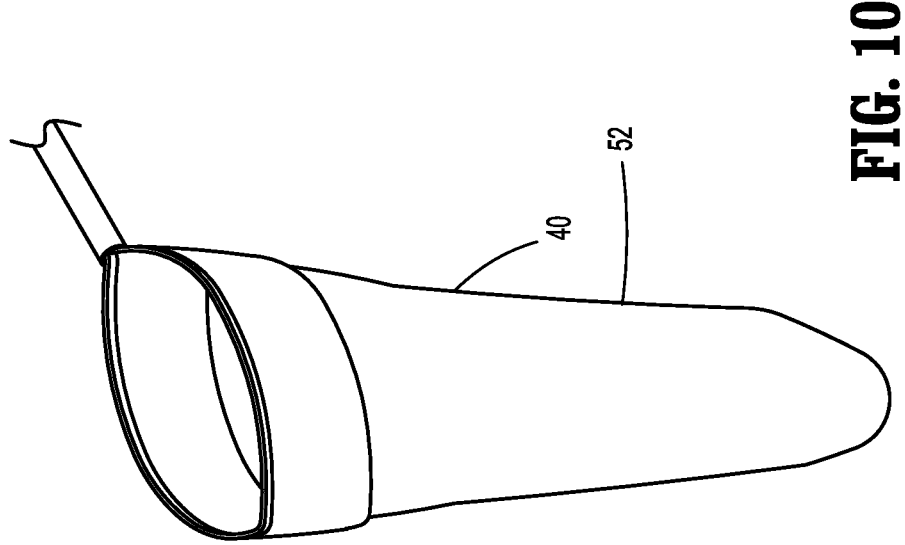
FIG. 10 is a side perspective view of the specimen bag shown in FIG. 1, where a first fold and a second fold of the specimen bag have unfolded as depicted in FIG. 7, producing a specimen bag of a second size.

If, however, the size of a tissue specimen to be removed from a patient cannot fit into the adjustable volume specimen bag 40 of the first size "S1", then the clinician will exert greater tension to pull the release string 70 so that the knot 80 at the distal portion 72 of the release string 70 passes through the first hole 56a in the first flange 54a on the second fold 50b and continue proximally pulling the release string 70 so that the knot 80 at the distal portion 70 of the release string 70 passes through the remaining holes 56b in the flanges 54b extending from the second fold 50b, as well as the holes 62 in the flanges 60 on the inner surface 52 of the adjustable volume specimen bag 40 adjacent the second fold 50b, until the knot 80 reaches the first hole 56a in the first flange 54a on the third fold 50c. Once the release string 70 passes through the remaining holes 56b associated with the second fold 50b, the second fold 50b is no longer held in place by the release string 70 and unfolds to form the adjustable volume specimen bag 40 of a second size "S2". (FIG. 10).

The first hole 56a extending from the first flange 54a on the third fold 50c will stop the knot 80 at the distal portion 72 of the release string 70 from passing therethrough, at which point the clinician will decide whether or not to continue to proximally pull the release string 70 to increase the volume of the adjustable volume specimen bag 40. In this case, the knot 80 topping the movement of the release string 70 at the first hole 56a in the first flange 54a on the third fold 50c provides the clinician with feedback of the expansion of the adjustable volume specimen bag 40.

If the size of a tissue specimen to be removed from a patient can fit into the adjustable volume specimen bag 40 of the second size "S2", then the clinician will stop proximally pulling the release string 70, and the specimen retrieval device 10, having the tissue specimen within the adjustable volume specimen bag 40, may be removed from the patient.

Figure 11:
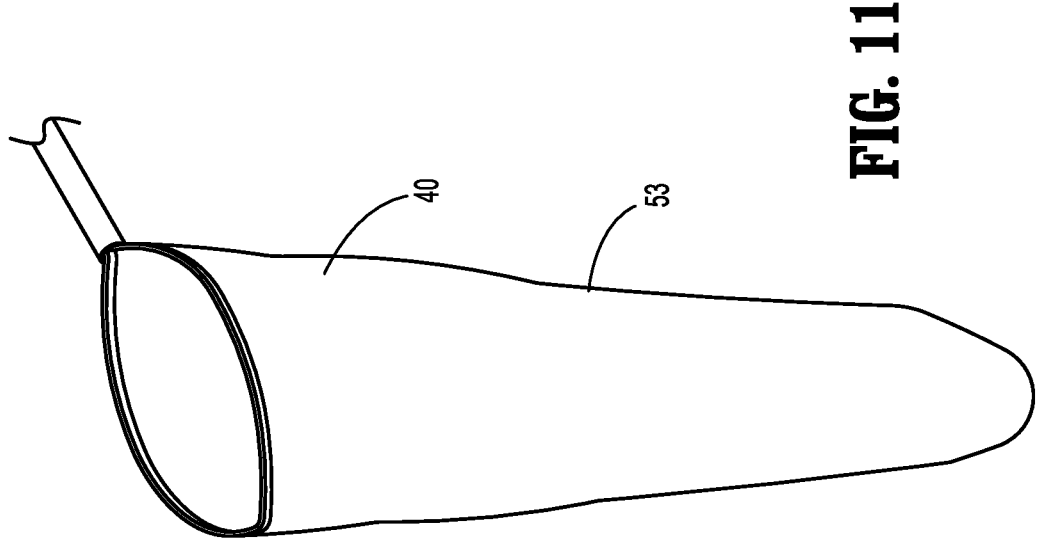
FIG. 11 is a side perspective view of the specimen bag shown in FIG. 1, where a first fold, a second fold, and a third fold of the specimen bag have unfolded as depicted in FIG. 7, producing a specimen bag of a third size.

If, however, the size of a tissue specimen to be removed from a patient cannot fit into the adjustable volume specimen bag 40 of the second size "S2", then the clinician will exert greater tension to pull the release string 70 so that the knot 80 at the distal portion 72 of the release string 70 passes through so that the knot 80 at the distal portion 72 of the release string 70 passes through the first hole 56a in the first flange 54a on the third fold 50c and continue proximally pulling the release string 70 so that the knot 80 at the distal portion of the release string 70 passes through the remaining holes 56b in the flanges 54b extending from the third fold 50c, as well as the holes 62 in the flanges 60 on the inner surface 52 of the adjustable volume specimen bag 40 adjacent the third fold 50c. Once the release string 70 passes through the remaining holes 56b associated with the third fold 50c, the third fold 50c is no longer held in place by the release string 70 and unfolds to form the adjustable volume specimen bag 40 of a third size "S3". (FIG. 11).

As depicted in FIGS. 6-11, as the adjustable volume specimen bag 40 only has three folds, once the third fold 50c unfolds to form the adjustable volume specimen bag 40 of a third size "S3", the adjustable volume specimen bag 40 is fully expanded to its largest size. The tissue specimen may then be placed within the adjustable volume specimen bag 40 and removed from the patient.

As noted above, while the adjustable volume specimen bag 40 depicted in FIGS. 6-11 has three folds, other configurations, having more or less folds, are contemplated. Where the adjustable volume specimen bag 40 has multiple folds, for example five folds, the adjustable volume specimen bag 40 permits the formation of a specimen bag of varying volumes, such as 250 ml, 500 ml, 1000 ml, 1200 ml and 1500 ml, all from a single starting specimen retrieval device 10 having the adjustable volume specimen bag 40 of the present disclosure.

Kits of the present disclosure may include both the specimen retrieval device described above, as well as trocars, graspers, vacuum sources (tubes), combinations thereof, and the like. In some embodiments, these additional devices, such as graspers and/or vacuum sources, may be used to break up the tissue specimen in the specimen bag prior to removing the specimen retrieval device from the body cavity.

Once the specimen retrieval device of the present disclosure has been removed from the patient's body, any tissue specimen may be removed from the adjustable volume specimen bag 40 for further examination and the adjustable volume specimen bag 40 may be discarded.

The specimen retrieval devices of the present disclosure permit the use of a single device with the adjustable volume specimen bag in a variety of procedures. During laparoscopic surgery, current specimen retrieval devices come with multiple bags of different sizes, which require the clinician to guess as to which one will be of sufficient size to remove the tissue specimen of interest. If the clinician guesses wrong, and the first bag introduced into a patient is too small, the specimen retrieval device has to be removed, and a new, larger specimen bag has to then be introduced into the patient. Thus, in accordance with the present disclosure, the removal of bags and inserting new bags is not required, thereby avoiding surgical delays. Moreover, unused bags are not wasted.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A specimen retrieval device comprising:
a tubular body defining a longitudinal bore, the tubular body having a proximal portion, a distal portion, and a hand grip supported on the proximal portion of the tubular body;
an inner shaft having a proximal portion, a distal portion, an actuation handle supported on the proximal portion of the inner shaft, and a support member extending from a distal portion of the inner shaft;
a specimen bag supported on the support member at the distal portion of the inner shaft, the specimen bag including an open end, a body, a closed portion, and an inner surface having flanges attached thereto, each flange having a hole therein, the body of the specimen bag including a plurality of folds between the open end and the closed portion, the plurality of folds each having flanges extending therefrom, each flange having a hole therein, and the plurality of folds being movable from a folded state to an unfolded state to increase a volume of the specimen bag; and
a release string secured to the plurality of folds, the release string movable from a non-actuated position to an actuated position to sequentially release at least one of the plurality of folds from the folded state to the unfolded state to increase the volume of the bag.

2. The specimen retrieval device of claim 1, wherein the release string has a knot at a distal portion thereof.

3. The specimen retrieval device of claim 1, wherein a first hole in a first flange extending from each of the plurality of folds furthest from the distal portion of the inner shaft is of a smaller diameter compared with the holes in the remaining flanges extending from the plurality of folds.

4. The specimen retrieval device of claim 1, wherein the plurality of folds is from two folds to ten folds.

5. The specimen retrieval device of claim 1, wherein the plurality of folds includes two folds.

6. The specimen retrieval device of claim 1, wherein the plurality of folds includes three folds.

7. The specimen retrieval device of claim 1, wherein the plurality of folds includes five folds.

8. The specimen retrieval device of claim 7, wherein the adjustable volume specimen bag permits the formation of a specimen bag of varying volumes of 250 ml, 500 ml, 1000 ml, 1200 ml and 1500 ml.

9. The specimen retrieval device of claim 1, wherein the support member includes a pair of resilient fingers which support the specimen bag and open the open end of the specimen bag in the deployed state.

10. The specimen retrieval device of claim 9, wherein the resilient fingers are positioned adjacent the open end of the specimen bag to open the specimen bag when the specimen retrieval device is in the deployed state.

11. A method comprising:
introducing the tubular body of the specimen retrieval device of claim 1 through a body opening into a body cavity;
moving the inner shaft including the support member within the longitudinal bore of the tubular body to position the specimen bag supported on the support member within the body cavity; and
withdrawing the release string from the specimen bag to incrementally increase the volume of the specimen bag.

12. The method of claim 11, wherein withdrawing the release string from the specimen bag includes proximally pulling the release string so that the release string passes through the holes on the flanges extending from the plurality of folds on the specimen bag and the holes on the flanges extending from the inner surface of the specimen bag.

13. The method of claim 12, wherein withdrawing the release string from the specimen bag includes proximally pulling the release string so that the release string passes through the holes on the flanges extending from at least one fold of the plurality of folds on the specimen bag and the holes on the flanges extending from the inner surface of the specimen bag.

14. The method of claim 11, further comprising:
passing a tissue specimen through the opening of the specimen bag into the specimen bag; and
removing the specimen retrieval device from the body cavity.

15. The method of claim 14, further comprising closing the opening of the specimen bag before removing the specimen retrieval device from the body cavity.

16. The method of claim 15, wherein closing the opening of the specimen bag occurs by proximally pulling a pull string extending about the opening of the specimen bag.

* * * * *